(12) United States Patent
Menne et al.

(10) Patent No.: US 6,533,792 B2
(45) Date of Patent: Mar. 18, 2003

(54) DEVICE FOR REMOVAL OF CALCULI

(75) Inventors: Andreas Menne, Meersburg (DE); Wolfgang Merkle, Meersburg (DE)

(73) Assignee: Ferton Holding, S.A. (CH)

( * ) Notice: Subject to any disclaimer, the term of this patent is extended or adjusted under 35 U.S.C. 154(b) by 0 days.

(21) Appl. No.: 09/878,110

(22) Filed: Jun. 8, 2001

(65) Prior Publication Data

US 2002/0010478 A1 Jan. 24, 2002

(30) Foreign Application Priority Data

Jun. 15, 2000 (DE) .......................... 100 29 582

(51) Int. Cl.[7] .............................. A61B 17/22
(52) U.S. Cl. ...................................... 606/128
(58) Field of Search ................. 606/128, 127; 128/660.03; 604/22

(56) References Cited

U.S. PATENT DOCUMENTS 5,065,762 A * 11/1991 Ifflaender et al.
5,160,336 A    11/1992 Favre
5,741,272 A *  4/1998 Kuhne
5,836,897 A * 11/1998 Sakurai et al.

FOREIGN PATENT DOCUMENTS

| DE | 3429487 C2 | 2/1986 |
| EP | 0421285 B1 | 11/1994 |
| EP | 0280088 B1 | 4/1995 |

* cited by examiner

*Primary Examiner*—Ismael Izaguirre
(74) *Attorney, Agent, or Firm*—Ostrolenk, Faber, Gerb & Soffen, LLP

(57) ABSTRACT

A device for removing calculi by using an intracorporeal lithotripter comprises a single metallic probe or sonotrode which for the fragmentation of calculi is connected with an electrically controlled ultrasonic transducer for generating longitudinal oscillations which alternatively may be switched to the generation of shock or pressure waves by a pulse wave stimulated oscillation of the metallic probe or sonotrode.

13 Claims, 1 Drawing Sheet

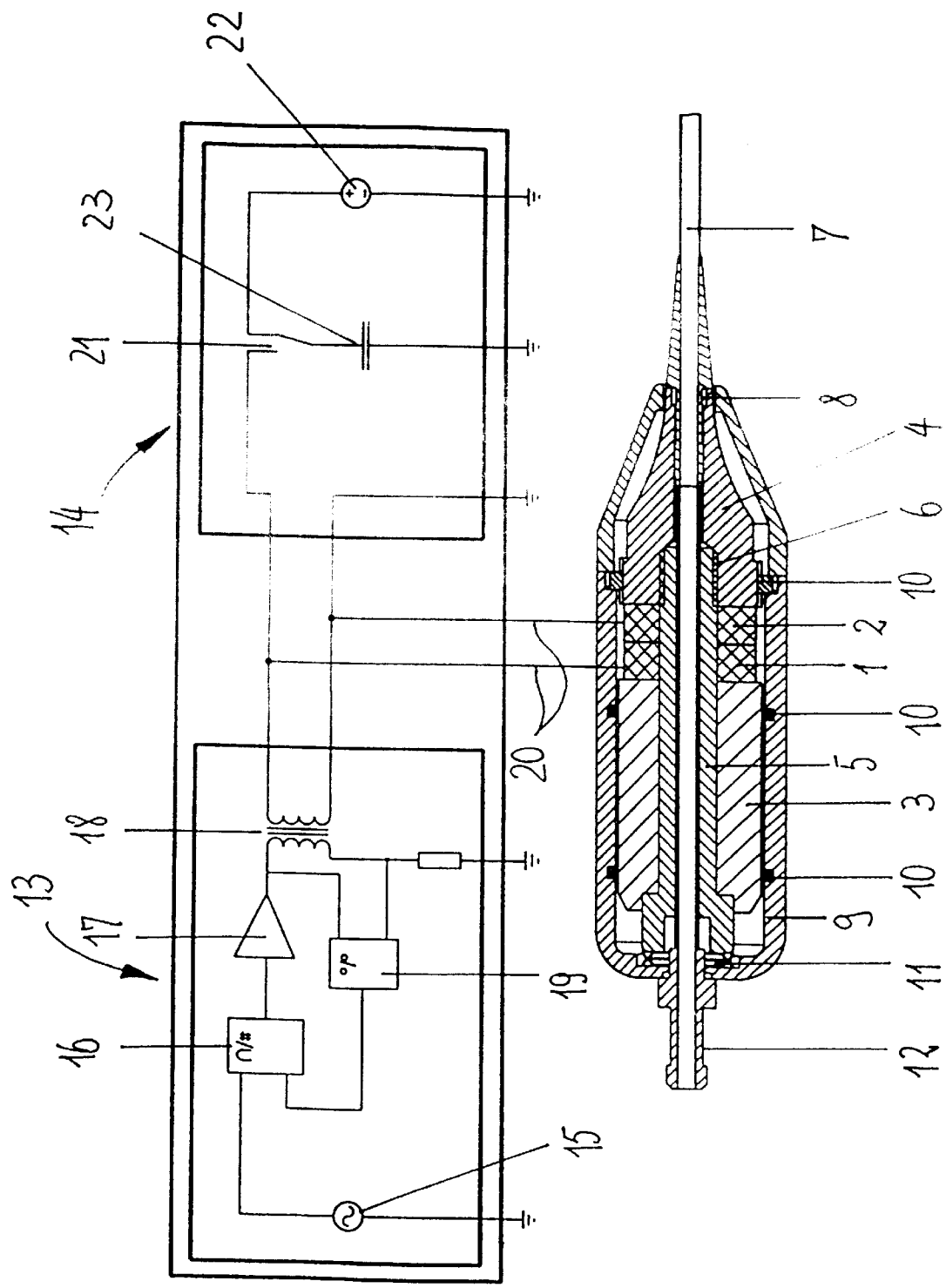

DEVICE FOR REMOVAL OF CALCULI

FIELD OF THE INVENTION

This invention relates to a device for removal of calculi by using an intracorporeal lithotripter.

BACKGROUND OF THE INVENTION

When removing calculi from body hollows it becomes necessary in general to crash first in situ those calculi which although still suitable for allowing a natural exit or drainage exceed a predetermined size. It therefore will be necessary to crash or fragment any overdimensioned calculi and to generate particles of a more or less minute size to thereby allow such minimised particles to being spontaneously removed from the body hollow. The minimisation is carried out by acting on the calculi with compressive and tensional forces which in the field of intracorporeal lithotripsy are exercised with the distal end of a metallic probe serving as a wave guide. Such forces result in a blasting-off of fragments from the surface of a calculus for effecting its crashing. However, when fragmenting calculi in this way there exists in general the problem of providing suitable energy transport or energy transfer specifically to those calculi which are to be minimised by avoiding at the same time any disturbing and rather dangerous side effects on the human tissue which therefore should not serve as a backing during such a fragmentation of calculi.

The European Patent EP 0 421 285 B1 discloses a device for removal of calculi by using an intracorporeal lithotripter. The device comprises a metallic probe or sonotrode which by means of an electrically controlled ultrasonic transducer generates longitudinal oscillations. When inserted into the operating passage of an endoscope as used for a fragmentation of calculi the distal end of the metallic probe or sonotrode when in contact with the calculi will crash the same by the transfer of those longitudinal oscillations. The ultrasonic transducer is composed of piezoceramic discs which are arranged within a surrounding casing between a reflector and a horn that are fastened to each other. For periodically oscillating the sonotrode the piezoceramic discs are controlled by a circuit arrangement which comprises a voltage-controlled oscillator the output signal of which is supplied to the piezoceramic discs via an output amplifier and an output transmitter. The circuit arrangement comprises a phase comparator for comparing the phases of the output voltage and of the output current of the output transmitter for generating a control voltage of the oscillator. With a device of this kind it will be possible to crash calculi into very fine fragments with a particle size which in general will not create any problems in sucking-off the calculi fragments through an axial hollow of the sonotrode and extending at its proximal end to an interconnected suction duct which is passed through the ultrasonic transducer. Any minimisation of calculi by means of an intracorporeal lithotripter operating with an ultrasonic transducer must be considered, however, as relatively time-consuming since for a careful handling of the lithotripter at the distal end of the tubular sonotrode it will only be allowable to use ultrasonic frequencies of about 20 to 25 kHz with amplitudes of about 50 $\mu$m for avoiding any damages of the human tissue. There will also be exist certain complications with calculi of a harder consistency which will not allow, any spontaneous peeling with such frequencies and amplitudes at the tip of the sonotrode. The operational treatment will accordingly either last very long or will even be impossible.

The European Patent EP 0 317 507 B1 discloses a lithotripter comprising a metallic probe the proximal end of which is arranged for being hit periodically by a pneumatically driven impact member or projectile resulting in an impact energy which is transported along the metallic probe as far as to its distal end so that any calculus when contacted with the tip of the probe will be fragmented under the action of shock or pressure waves. Such shock or pressure wave lithotripters which with alternative designs may also be provided with an electric drive for the impact member or projectile are constructed in general as relatively simple units having nevertheless very high efficiencies with the fragmentation of calculi although it has to be conceded that the handling of such shock or pressure wave lithotripters is still somewhat time-consuming in the context of providing particles that may be spontaneously sucked-off.

SUMMARY OF THE INVENTION

An object of the present invention is to provide a device for removal of calculi by using an intracorporeal lithotripter which will allow a more flexible fragmentation of calculi under consideration of the advantages and the disadvantages of the presently known methods when using lithotripters of the kind as above described.

In accordance with the present invention a device for removal of calculi by using an intracorporeal lithotripter of the kind as referred above is provided which is characterised by the features of the claims.

The present invention offers the possibility for operating a device for removing calculi in accordance with two different operation principles. The one operation principle or mode thereby substantially corresponds with its periodically stimulated oscillation of a metallic probe or sonotrode with the operation principle of the hitherto known ultrasonic wave lithotripters. It operates with the generation of a stationary wave causing sinusoidal motion in axial direction of the distal end of the wave guide so that a fragmentation of calculi will be effected mechanically. The alternative operative principle with a pulse wave stimulated oscillation of the metallic probe or sonotrode as effected by a simple change-over of the switch will generate on the other side a single pulse which will instantaneously expand the at least one piezoceramic disc of the ultrasonic transducer. This will result in the generation of a single shock or pressure wave in the metallic probe or sonotrode to thereby generate a single pressure pulse of a high power which will be transferred via the distal end of the wave guide to the calculus which is in contact with the same. Since such a pressure pulse is obtained within a relatively small time window this will undoubtedly result in a transfer of a much higher power than in case of a periodic stimulated oscillation so that with this alternative operating mode the fragmentation of calculi will become more effective than in case of the hitherto known shock wave lithotripers.

Other objects, features and advantages of the present invention will become apparent from reading the following description of a preferred embodiment of a device according to the present invention.

BRIEF DESCRIPTION OF THE DRAWINGS

The invention will now be described by way of example with reference to the accompanying drawing which shows a sectional view of the device together with a diagram showing the circuitry of its ultrasonic transducer.

DETAILED DESCRIPTION OF THE PREFERRED EMBODIMENT

The device for removal of calculi as shown in the drawing comprises an electrically controlled ultrasonic transducer which is designed as a piezoelectric transducer having two piezoceramic discs 1 and 2 that are arranged between a reflector 3 and a horn 4. The arrangement comprising these elements of the ultrasonic transducer are fixedly interconnected by means of a hollow fastening stud bolt 5 which is axially passed through a center hole of the two ceramic discs 1, 2 and the reflector 3 for being screw connected with the horn 4 at a threaded portion 6. The horn 4 is further screw connected with a tubular metallic probe or sonotrode 7 at a screw portion 8 so that the hollow of the fastening stud bolt 5 is axially aligned with the hollow of the metallic probe or sonotrode 8.

The ultrasonic transducer comprising those elements as mentioned before and held together by the fastening stud bolt 5 is arranged within a casing 9. This casing 9 is formed of two parts having a partition plane which is located in the vicinity of the horn 4 so that the fastening stud bolt 5 also allows an elastic fastening of the ultrasonic transducer with respect to the casing via elastic supporting means in the form of O-rings 10 and of a packing 11 which are supporting the ultrasonic transducer on the casing 9. The hollow fastening stud bolt 5 is connected at its outer end with a suction duct connection 12 so that any fragments of calculi which will be generated with the distal end of the metallic probe or sonotrode 7 may be sucked-off via the hollow of the metallic probe or sonotrode and the axially aligned hollow of the fastening stud bolt 5. It is to be understood that the metallic probe or sonotrode 7 is arranged for being inserted into the operating passage of an endoscope whereby its distal end will project forwardly of the horn 4 of the ultrasonic transducer.

The two piezoceramic discs 1, 2 are coupled with a first circuit system 13 for stimulating periodic oscillations of the metallic probe or sonotrode 7 and with a second circuit system 14 for stimulating a pulse wave oscillation of one and the same metallic probe or sonotrode. The first circuit system 13 comprises a voltage-controlled oscillator 15 which is connected via a voltage-and-frequency-converter 16 and an interconnected output amplifier 17 to an impedance transformer 18. The impedance transformer 18 is coupled with the voltage-and-frequency-converter 16 via a phase comparator 19 which is arranged for comparing the phases of the output voltage and the output current of the impedance transformer 18 to thereby generate a control voltage for the oscillator 15. The first circuit system 13 therefore generates with its output signal a periodic oscillation stimulation of the metallic probe or sonotrode 7 via connecting lines 20 leading to the two piezoceramic discs.

The two piezoceramic discs 1, 2 are on the other side also connected with the second circuit system 14 which is arranged for stimulating a pulse wave oscillation of the metallic probe or sonotrode 7. This second circuit system 14 comprises a voltage source 22 and a capacitor 23 which in a first control position of an interconnected change-over switch 21 is loaded by the voltage source 22. When switched to a second control position of the change-over switch 21 the capacitor 23 will then be discharged for stimulating the metallic probe or sonotrode 7 with a single shock or pressure wave by means of the two piezoceramic discs 1, 2. Since the output signal of the second circuit system 14 will be of a much higher power in comparison with the output signal which will be supplied by the first circuit system 13 the two piezoceramic discs 1, 2 will therefore be instantaneously expanded by this much higher power so that a single shock or pressure wave will accordingly be generated in the metallic probe or sonotrode 7 resulting in a corresponding single shock or pressure pulse which will be transferred by the distal end of the sonotrode to any calculus which is being kept in contact with the same when the fragmentation of calculi proceeds.

For obtaining optimum results for such a pulse wave stimulated oscillation of the metallic probe or sonotrode 7, the horn 4 of the ultrasonic transducer as well as the sonotrode 7 should comprise a material of substantially the same acoustic impedance. As preferred materials high-grade steel or titanium should be used. The horn 4 should be further provided with an enveloping surface which tapers in the axial direction substantially to the cross-section where the metallic probe or sonotrode 7 is screw-connected with the horn 4. It should of course be understood that the elastic means 10, 11 which are provided for supporting the ultrasonic transducer on the surrounding casing should be formed such as to provide optimum operating conditions both for the periodic and the pulse wave stimulated oscillation of the metallic probe or sonotrode. In addition to the change-over switch 21 there could be further provided separate change-over switch control means (not shown) for allowing a change-over between two separate line connections (not shown) of the two circuit systems 13, 14 and the two piezoceramic discs 1, 2 to which further piezoceramic discs could be added.

We claim:

1. A device for removing calculi by using an intracorporeal lithotripter, comprising:

a metallic probe or sonotrode serving as a wave guide and being inserted into an operating passage of an endoscope for a fragmentation of calculi via a distal end of said metallic probe or sonotrode;

an electrically controlled ultrasonic transducer for generating longitudinal oscillations, for being transferred to said metallic probe or sonotrode;

the ultrasonic transducer comprising at least one piezoceramic disc which is arranged between a reflector and a horn that carries said metallic probe or sonotrode, the arrangement being fixedly interconnected by a traversing fastening stud bolt;

the electrically controlled oscillations of said metallic probe or sonotrode as electrically controlled by said ultrasonic transducer being switchable between a periodically stimulated oscillation and a pulse wave stimulated oscillation of said metallic probe or sonotrode;

wherein two separate first and second circuit systems are provided for controlling said periodic and said pulse wave stimulated oscillations, respectively, of said metallic probe or sonotrode, wherein a first circuit system for controlling the periodic oscillation of the metallic probe or sonotrode comprises a voltage-controlled oscillator which is connected via a voltage-to-frequency converter and an interconnected output amplifier to an impedance transformer, and a phase comparator which is arranged for comparing the phases of the output voltage and the output current of the impedance transformer to thereby generate a control voltage for the oscillator; and wherein a second circuit system for controlling the pulse wave stimulated oscillation of the metallic probe or sonotrode comprises a voltage source and a capacitor which are interconnected via a change-over switch, said change-over switch being arranged for coupling the second circuit system with the ultrasonic transducer.

2. The device according to claim 1, wherein said capacitor is loaded in a first control position of said change-over switch and when switched to a second control position of the switch is coupled with said ultrasonic transducer, the capacitor being discharged in the second control position for stimulating said metallic probe or sonotrode with a single shock or pressure wave.

3. The device according to claim 1, wherein said horn has an enveloping surface which tapers in the axial direction substantially to the cross-section of a screw connection between the horn and the metallic probe or sonotrode.

4. The device according to claim 1, wherein said fastening stud bolt is hollow and is axially aligned by this hollow with a hollow of a tubular metallic probe or sonotrode to thereby interconnect said distal end of the metallic probe or sonotrode with a suction duct connection at a rearward end of the hollow fastening stud bolt.

5. The device according to claim 1, wherein said metallic probe or sonotrode and said horn comprise a material of substantially the same acoustic impedance.

6. The device according to claim 1, wherein said first and second circuit systems are connected with said at least one piezoceramic disc of the ultrasonic transducer via separate connecting lines that are interconnected by a change-over switch control.

7. A device for removing calculi by using an intracorporeal lithotripter, comprising:
- a metallic probe or sonotrode serving as a wave guide and being inserted into an operating passage of an endoscope for a fragmentation of calculi via a distal end of said metallic probe or sonotrode;
- an electrically controlled ultrasonic transducer for generating longitudinal oscillations, for being transferred to said metallic probe or sonotrode;
- the ultrasonic transducer comprising at least one piezoceramic disc which is arranged between a reflector and a horn that carries said metallic probe or sonotrode, the arrangement being fixedly interconnected by a traversing fastening stud bolt;
- the electrically controlled oscillations of said metallic probe or sonotrode as electrically controlled by said ultrasonic transducer being switchable between a periodically stimulated oscillation and a pulse wave stimulated oscillation of said metallic probe or sonotrode;
- wherein said arrangement comprising said ultrasonic transducer and said fastening stud bolt is supported on a surrounding casing by an elastic support.

8. The device according to claim 7, wherein two separate first and second circuit systems are provided for controlling said periodic and said pulse wave stimulated oscillations, respectively, of said metallic probe or sonotrode,
- wherein a first circuit system for controlling the periodic oscillation of the metallic probe or sonotrode comprises a voltage-controlled oscillator which is connected via a voltage-to-frequency converter and an interconnected output amplifier to an impedance transformer, and a phase comparator which is arranged for comparing the phases of the output voltage and the output current of the impedance transformer to thereby generate a control voltage for the oscillator; and
- wherein a second circuit system for controlling the pulse wave stimulated oscillation of the metallic probe or sonotrode comprises a voltage source and a capacitor which are interconnected via a change-over switch, said change-over switch being arranged for coupling the second circuit system with the ultrasonic transducer.

9. A device according to claim 8, wherein said first and second circuit systems are connected with said at least one piezoceramic disc of the ultrasonic transducer via separate connecting lines that are interconnected by a change-over switch control.

10. The device according to claim 8, wherein said capacitor is loaded in a first control position of said change-over switch and when switched to a second control position of the switch is coupled with said ultrasonic transducer, the capacitor being discharged in the second control position for stimulating said metallic probe or sonotrode with a single shock or pressure wave.

11. A device according to claim 7, wherein said horn has an enveloping surface which tapers in the axial direction substantially to the cross-section of a screw connection between the horn and the metallic probe or sonotrode.

12. A device according to claim 7, wherein said fastening stud bolt is hollow and is axially aligned by this hollow with a hollow of a tubular metallic probe or sonotrode to thereby interconnect said distal end of the metallic probe or sonotrode with a suction duct connection at a rearward end of the hollow fastening stud bolt.

13. A device according to claim 7, wherein said metallic probe or sonotrode and said horn comprise a material of substantially the same acoustic impedance.

* * * * *